United States Patent [19]

Inoue et al.

[11] Patent Number: 4,533,732
[45] Date of Patent: Aug. 6, 1985

[54] 3-PROPIONYLSALICYLIC ACID DERIVATIVES AND PROCESS FOR THE PREPARATION OF THE SAME

[75] Inventors: Hiroshige Inoue, Osaka; Kenichi Fukushima, Arita; Ikuzo Nishiguchi, Hirakata, all of Japan

[73] Assignees: Yamamoto Chemical Industrial Company, Limited, Wakayama; Osaka Municipal Government, Osaka, both of Japan

[21] Appl. No.: 538,016

[22] Filed: Sep. 30, 1983

[30] Foreign Application Priority Data

Sep. 30, 1982 [JP] Japan ................. 57-171304

[51] Int. Cl.³ .................... C07D 295/14; C07C 65/10; C07C 69/88
[52] U.S. Cl. .................... 544/172; 544/399; 546/238; 548/573; 560/53; 562/463; 549/403; 514/869; 514/929
[58] Field of Search ............... 544/172, 399; 546/238; 548/573; 560/53; 562/463

[56] References Cited

FOREIGN PATENT DOCUMENTS 757821 10/1970 Belgium .

Primary Examiner—Robert W. Ramsuer
Attorney, Agent, or Firm—Armstrong, Nikaido, Marmelstein & Kubovcik

[57] ABSTRACT

This invention relates to derivatives of 3-propionylsalicylic acid represented by the formula (1)

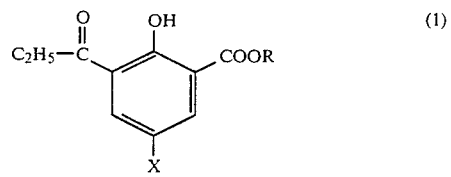

wherein R represents a hydrogen atom, a lower alkyl group or a group

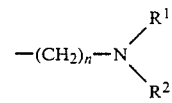

(wherein $R^1$ and $R^2$ represent a lower alkyl group or $R^1$ and $R^2$, when taken together with the nitrogen atom to which they are attached, may form a heterocyclic ring with or without an intervening hetero atom, and n is an integer of 1 to 4), and X represents a hydrogen atom or a halogen atom, R being the group

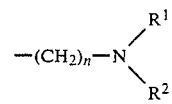

when X is a hydrogen atom.

This invention also relates to processes for preparing the same.

11 Claims, No Drawings

3-PROPIONYLSALICYLIC ACID DERIVATIVES AND PROCESS FOR THE PREPARATION OF THE SAME

This invention relates to derivatives of 3-propionylsalicylic acid and to processes for preparing the same.

The 3-propionylsalicylic acid derivatives of the present invention are novel compounds undisclosed in literature and represented by the formula (1)

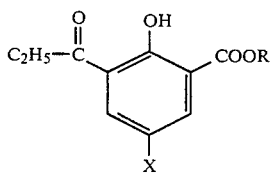

wherein R represents a hydrogen atom, a lower alkyl group or a group

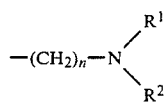

(wherein $R^1$ and $R^2$ represent a lower alkyl group or $R^1$ and $R^2$, when taken together with the nitrogen atom to which they are attached, may form a heterocyclic ring with or without an intervening hetero atom, and n is an integer of 1 to 4.), and X represents a hydrogen atom or a halogen atom, R being the group

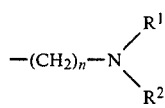

when X is a hydrogen atom.

The compounds of this invention represented by the formula (1) are useful as intermediates for synthesizing derivatives of 3-methylflavone-8-carboxylic acid which have pharmacodynamic actions as described below and which are represented by the formula (6)

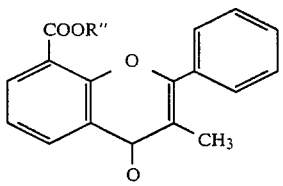

wherein R'' represents a group

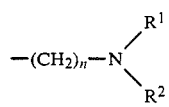

(wherein $R^1$ and $R^2$ are as defined above). The compounds of the formula (6) have an activity of coronary vasodilation and another activity of increasing the coronary blood flow. With these activities, the compounds find applications in treating angina pectoris and in preventing the paroxysm of myocardial infarction and are also usable as a therapeutic agent for inhibiting the increase in a capacity of the bladder, as a remedial agent for treating the pollakisuria anosognosia or as a diuretic having an activity of relaxation for convulsion of smooth muscle of the low urinary tract.

Processes for preparing the compounds of the formula (6) are known, as disclosed, for example, in U.S. Pat. No. 2,921,070 and in Japanese Examined Patent Publication No. 7953/1966. However, these conventional processes have drawbacks as stated below, hence commercially inappropriate. The process described in the U.S. patent attempts to successively produce compounds (II), (III) and (IV) and eventually a compound (V) [which corresponds with the compound of the formula (6)], as shown below in the following reaction equations.

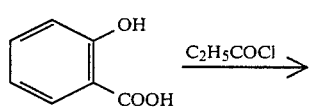

(I)

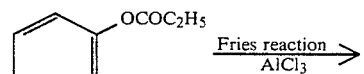

(II)

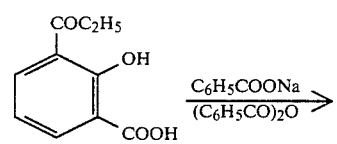

(III)

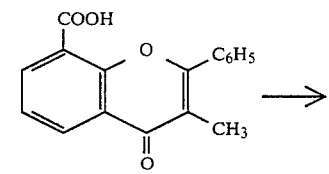

(IV)

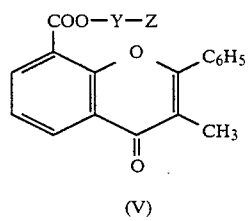

(V)

In the foregoing reaction equations, Y represents a divalent, straight alkylene chain having from 2 to 3 carbon atoms and Z represents dimethylamino, diethylamino, di-n-propylamino, diisopropylamino, piperidino or morpholino.

According to the process shown above, however, Fries reaction is carried out to prepare the compound (III) from the compound (II), resulting in the production of the compound (III) in an extremely small amount and the isomer of the compound (III), 2-hydroxy-5-propionylbenzoic acid, in a markedly large amount. This leads to the preparation of the compound (V) in trace amount such that the production of the compound (V) can be barely detected. The manufacture of 2-hydroxy-5-propionylbenzoic acid in large amounts by subjecting the compound (II) to Fries reaction is disclosed, for example, in German patent specification No. 2,059,269 and in British patent specification No. 1,343,118.

The process stated in Japanese Examined Patent No. 7953/1966 employs 3-allyl-2-hydroxypropiophenone (VI) as the starting material, attempting to prepare compounds (VII) and (IV) and finally the compound (V), as shown in the following reaction equations.

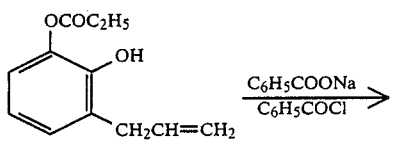

(VI)

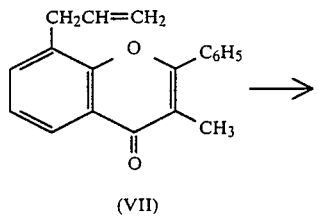

(VII)

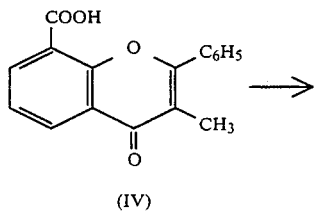

(IV)

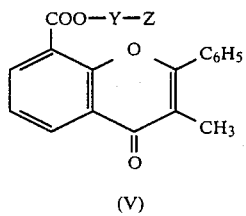

(V)

In the foregoing reaction equations, Y and Z are as defined above.

The 3-allyl-2-hydroxypropiophenone (VI) to be used as the starting material in the process is not easily available, because as apparent from the following reaction equations [Org. Synth. coll., 2,543 and Journal of the Pharmaceutical Society of Japan, 74, 48 (1954)], it is difficult to prepare the compound (VI) efficiently from propiophenone (VIII) although the compound (VIII) is readily available.

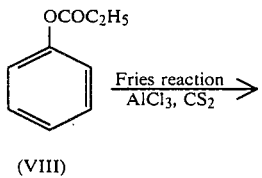

(VIII)

-continued

[Structures IX and X shown]

(IX)   (X)

[Structure IX shown]

(IX)

[Structure XI with Fries reaction / AlCl₃ arrow]

(XI)

[Structure VI shown]

(VI)

In the above-mentioned process, the compound (VIII) undergoes Fries reaction which produces, in addition to the compound (IX), the compound (X) as a by-product in a larger amount which is difficult to separate from the compound (IX). The production of this by-product involves a cumbersome separating procedure and results in the preparation of the compound (VI) with reduced purity in a lower yield. In short, the process disclosed in Japanese Examined Patent Publication No. 7953/1966 gives the compound (V) in a yield as low as 4 to 5% based on the readily available compound (VIII).

An object of this invention is to provide the novel derivatives of 3-propionylsalicylic acid represented by the formula (1) which are useful as intermediates for synthesizing derivatives of 3-methylflavone-8-carboxylic acid of the formula (6).

Another object of the invention is to provide novel processes for preparing the derivatives of 3-propionylsalicylic acid represented by the formula (1).

Other objects and other features of the invention will become apparent from the following description.

Examples of lower alkyl groups represented by R in the formula (1) are methyl, ethyl, n-propyl, isopropyl, n-butyl and like alkyl groups having 1 to 4 carbon atoms. Examples of the groups $$-(CH_2)_n-N\begin{array}{c}R^1\\ \\R^2\end{array}$$

represented by R are dimethylaminomethyl, dimethylaminoethyl, diethylaminopropyl, diethylaminobutyl, di-n-propylaminomethyl, di-n-butylaminoethyl, morpholinomethyl, morpholinoethyl, piperidinomethyl, piperidinoethyl, piperidinopropyl, piperidinobutyl, 1-piperazinylmethyl, 1-piperazinylethyl, pyrrolidinomethyl, pyrrolidinoethyl, pyrrolidinopropyl, etc. Examples of halogen atoms represented by X are fluorine, chlorine, bromine, iodine, etc.

The derivatives of 3-propionylsalicylic acid represented by the formula (1) can be prepared by various processes. A preferred example of the processes is as given below.

Among the compounds of the formula (1), compounds represented by the formula (1a)

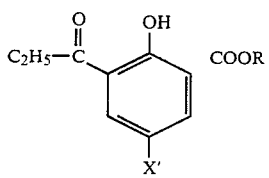

wherein X' is a halogen atom and R is as defined above, can be prepared by subjecting to Friedel-Crafts or Fries reaction propionyl halide and a salicylic acid derivative represented by the formula

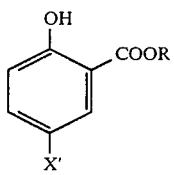

wherein R and X' are as defined above.

The foregoing Friedel-Crafts or Fries reaction is conducted in the presence of a suitable catalyst. Examples of catalysts useful in the Friedel-Crafts or Fries reaction include a wide variety of catalysts commonly used in this sort of reaction, such as aluminum chloride, ferric chloride, antimony pentachloride, boron trifluoride, zinc chloride, titanium chloride, boron fluoride, sulfuric acid, phosphoric acid, phosphoric anhydride, etc. The amount of such catalysts ranges usually from about 1 to about 4 moles, preferably from about 2 to about 3 moles, per mole of the compound of the formula (2). Examples of useful propionyl halides are propionyl chloride, propionyl bromide and the like. The propionyl halide is used in an amount which is not particularly limitative and which can be suitably selected over a wide range. The amount of the halide is in the range of usually about 1 to about 4 moles, preferably about 2 to about 3 moles, per mole of the compound of the formula (2). The reaction is conducted with or without a solvent, preferably in the absence of a solvent. Useful solvents include carbon disulfide, nitrobenzene, chloroform, carbon tetrachloride, etc. The solvent is employed in an amount substantially equal to that of the compound of the formula (2). The reaction is performed at a temperature ranging usually from room temperature to about 200° C., preferably from about 50° to about 100° C. and is completed in about 2 to about 10 hours.

The compound of the formula (2) to be used as the starting material in the foregoing reaction can be easily prepared by halogenating a salicylic acid represented by the formula (3)

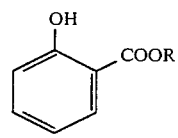

wherein R is as defined above. The halogenation is carried out by reacting the compound of the formula (3) with halogen in a suitable solvent at a temperature in the range of about 0° C. to room temperature for about 1 to about 6 hours. The amounts of the compound of the formula (3) and halogen are not particularly limited and can be determined over a wide range. The latter is used in an amount of usually about 1 to about 2 moles, preferably about 1 to about 1.5 moles, per mole of the former. It is preferred to use as a solvent chloroform which is used usually in an excess amount relative to the compound of the formula (3).

Among the compounds of the formula (1), compounds represented by the formula (1b)

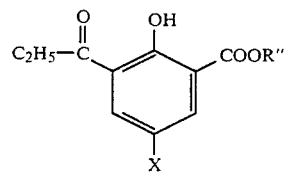

wherein R'' represents a group

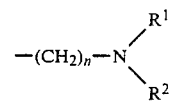

(wherein $R^1$, $R^2$ and n are as defined above) and X is as defined above can be prepared by reacting a derivative of 3-propionylsalicylic acid represented by the formula (1c)

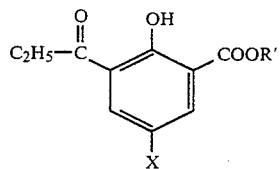

wherein R' represents a hydrogen atom or a lower alkyl group and X is as defined above with an amine represented by the formula (4)

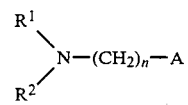

wherein A represents a halogen atom or a hydroxyl group, and $R^1$, $R^2$ and n are as defined above.

The reaction between the compound of the formula (1c) and the compound of the formula (4) is conducted in the presence of an alkali metal with or without a suitable solvent. Examples of useful solvents are chloroform, carbon tetrachloride and like hydrocarbon halogenides, benzene, toluene, xylene and like aromatic hydrocarbons, etc. The amounts of the compounds of the formulae (1c) and (4) are not particularly limited and can be determined over a wide range. The latter is used in an amount of usually about 1 to about 5 moles, preferably about 1.2 to about 2 moles, per mole of the former. Examples of useful alkali metals are sodium, potassium, etc. The amount of the alkali metal is usually about 0.05 to about 0.5 mole, preferably about 0.1 to about 0.3 mole, per mole of the compound of the formula (1c). The reaction is carried out usually at a temperature of usually about 0° to about 100° C., preferably about 20° to about 80° C., for about 3 to about 5 hours.

Among the compounds of the formula (1), compounds represented by the formula (1d)

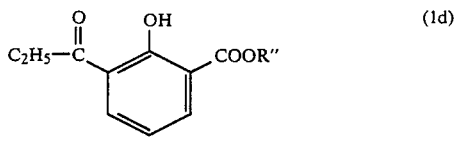

wherein R" is as defined above can be prepared by dehalogenating the compound of the formula (1b) wherein X is a halogen atom.

Examples of catalysts which can be used in dehalogenating the compound of the formula (1b) include a wide variety of catalysts heretofore known, such as palladium-carbon, palladium-asbestos, palladium-magnesium sulfate, Raney nickel, platinum black, etc. The amount of the catalyst is usually about 1 to about 10 wt.%, preferably about 3 to about 5 wt.%, based on the compound of the formula (1b). The dehalogenation is conducted in a suitable solvent such as methanol, ethanol, n-propanol, isopropanol, n-butanol, isobutanol or like lower aliphatic alcohol, ethyl acetate, butyl acetate, or like acetates, etc. It is preferred to incorporate in the reaction system sodium acetate, sodium propionate, sodium tartrate, sodium citrate or like alkali metal of fatty acid in order to collect the hydrogen chloride produced. The amount of the alkali metal of fatty acid is usually about 0.5 to about 2.5 moles per mole of the compound of the formula (1b). The reaction proceeds at a temperature of usually about 10° to about 100° C., preferably about 40° to about 80° C. and is completed usually in about 3 to about 10 hours.

The compound of the formula (1d) can be also prepared by a process comprising the steps of dehalogenating the compound of the formula (1c) wherein X is a halogen atom to provide a compound of the formula (5)

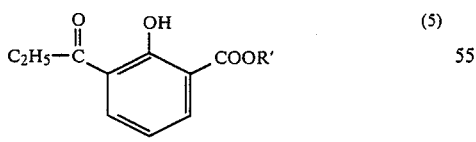

wherein R' is as defined above and reacting the compound of the formula (5) thus obtained with the amine of the formula (4).

The dehalogenation of the formula (1c) is carried out under the same conditions as those employed in dehalogenating the compound of the formula (1b). The reaction between the compound of the formula (5) and the amine of the formula (4) is performed under the same conditions as those employed in the reaction between the compound of the formula (1c) and the amine of the formula (4).

The contemplated compound obtained by each of the foregoing reactions can be separated from the reaction mixture and purified by a conventional method such as distillation, recrystallization, etc.

In any of the above-mentioned processes of the present invention, the reaction procedure is simple; a readily available compound is used as the starting material and the reaction quantitatively proceeds so that the contemplated compound of the formula (6) can be prepared with high purity of over 99.99% in a high yield of over 55% based on the compound of the formula (3).

The compounds of the present invention having the formula (1) are useful as intermediates for synthesizing the derivatives of 3-methylflavone-8-carboxylic acid of the formula (6), as shown in reaction equations given below, which derivatives are usable as therapeutic agents for inhibiting the increase in a capacity of the bladder, mitigating the irritability of the bladder and treating the pollakisuria-residual anosognosia.

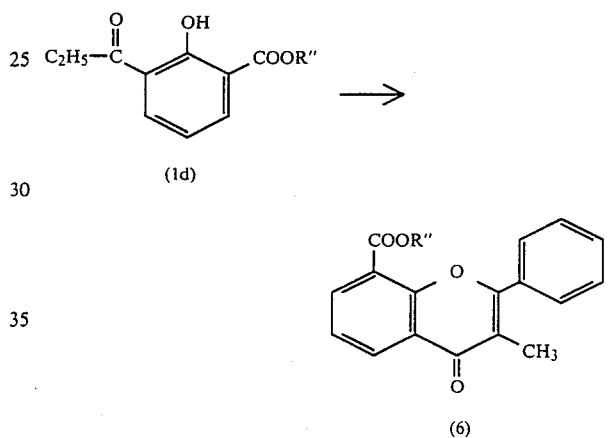

The reaction for preparing the compound of the formula (6) from the compound of the formula (1d) is effected by adding benzoyl chloride and sodium benzoate to the compound of the formula (1d) and heating the mixture. The amounts of the benzoyl chloride and sodium benzoate are each about 1 to about 8 moles per mole of the compound of the formula (1d). The heating temperature ranges usually from about 150° to about 200° C., preferably about 180° to about 195° C.

To clarify the features of the present invention, given below are examples and reference examples.

REFERENCE EXAMPLE 1

Synthesis of methyl 5-chlorosalicylate

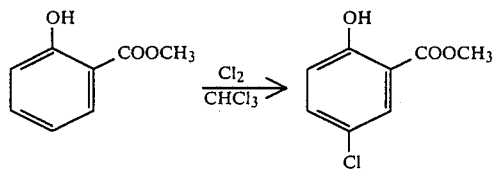

A 85.2 g quantity of chlorine gas was absorbed in a mixture of 152 g (1.0 mole) of methyl salicylate and 500 ml of chloroform at less than 20° C. over a period of 6 hours while the mixture was stirred. The resulting reaction mixture was washed with water and the chloroform was removed. The residue was subjected to fractional distillation at reduced pressure to provide 152 g (81.5%) of a fraction at 117° to 120° C. and 8 mmHg., M.P. 51° C.

REFERENCE EXAMPLE 2

Synthesis of methyl 5-bromosalicylate

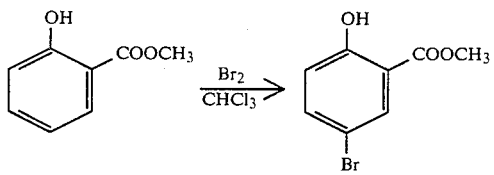

To a mixture of 152 g (1.0 mole) of methyl salicylate and 500 ml of chloroform were added dropwise with stirring a solution of 172 g (1.08 mole) of bromine in 300 ml of chloroform at about 10° C. over a period of 6 hours. After the addition, the mixture was stirred at the same temperature for 1 hour. The reaction mixture was washed with water and then with an aqueous solution of sodium bicarbonate. Removal of the solvent gave 230 g of substantially pure methyl 5-bromosalicylate in 99.6% yield, M.P. 59° to 61.5° C.

NMR (DMSO-$d_6$, δ, ppm) 8.30 (d, 1H), 8.09 (dd, 1H), 7.38 (d, 1H), 4.13 (s, 3H)

IR (KBr, cm$^{-1}$) 3200, 1690–1680

EXAMPLE 1

(a) Synthesis of methyl 5-chloro-3-propionylsalicylate

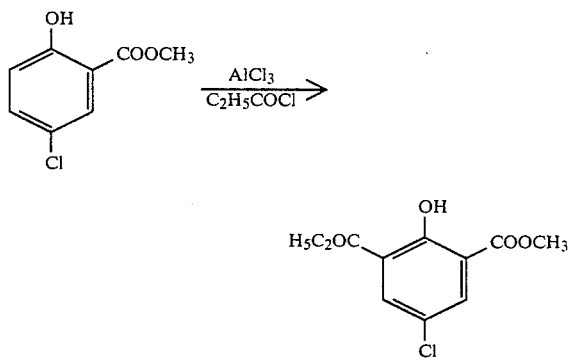

A 80.1 g (0.60 mole) quantity of anhydrous aluminum chloride was added in small amounts with stirring to a mixture of 37.3 g (0.20 mole) of methyl 5-chlorosalicylate and 46.3 g (0.50 mole) of propionyl chloride. The resulting mixture was maintained at room temperature for 1 hour and was heated at 80° C. at which the reaction was continued for 7 hours. After completion of the reaction, the reaction mixture was cooled and water was added thereto in small amounts to decompose the mixture. The resulting mixture was extracted with chloroform. The chloroform was recovered from the chloroform extract and the residue was subjected to distillation at reduced pressure to separate the same into the contemplated product (over 110° C./3 mmHg) and the unreacted material (105° to 110° C./3 mmHg). The fractionation gave 37.5 g of the contemplated product (in a yield of 98.4% based on the consumed amount of the methyl 5-chlorosalicylate) and 8.0 g of the unreacted substance. The purified product was found to have a melting point of 94.0° to 96.8° C. and the results of the chemical analysis are shown in Table 1 below.

(b) Synthesis of 5-chloro-3-propionylsalicylic acid

The methyl 5-chloro-3-propionylsalicylic acid obtained above in (a) was hydrolyzed to give 5-chloro-3-propionylsalicylic acid melting at 145.2° to 146.3° C. which was chemically analyzed with the results shown in Table 1 below.

EXAMPLE 2

Synthesis of ethyl 5-chloro-3-propionylsalicylate

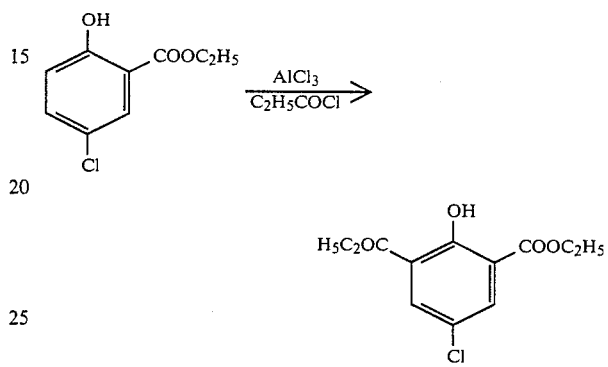

A 80.1 g (0.60 mole) quantity of anhydrous aluminum chloride was added in small amounts with stirring to a mixture of 40.1 g (0.20 mole) of ethyl 5-chlorosalicylate and 46.3 g (0.50 mole) of propionyl chloride. The resulting mixture was maintained at room temperature for 1 hour and heated at 80° C. to continue reaction at the same temperature for 7 hours. Thereafter, the reaction mixture was cooled and water was added in small amounts thereto to decompose the mixture. The contemplated product was extracted with chloroform. The chloroform was recovered from the extract and the residue was subjected to distillation and was separated into a product (over 115° C./3 mmHg) and the unreacted substance (105° to 115° C./3 mmHg). The product was obtained in an amount of 39.6 g and the unreacted substance in an amount of 8.5 g. A yield as calculated based on the consumed ethyl 5-chlorosalicylate was 98.0%. The purified product had a melting point of 53.0° to 54.5° C. The chemical analysis of the product was performed with the results shown in Table 1 below.

EXAMPLE 3

(a) Synthesis of methyl 5-bromo-3-propionylsalicylate

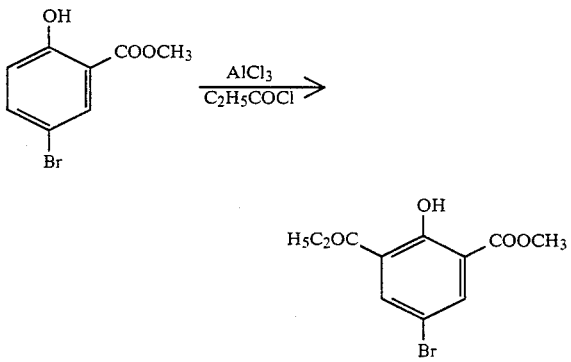

80.1 g (0.60 mole) quantity of anhydrous aluminum chloride was added in small amounts with stirring to a mixture of 46.2 g (0.20 mole) of methyl 5-bromosalicylate and 46.3 g (0.50 mole) of propionyl chloride. The resulting mixture was maintained at room temperature and was heated at 80° C. to undergo reaction for 7 hours. After cooling, water was added in small amounts to the reaction mixture to decompose the same. The solution was extracted with chloroform. After removing the solvent, the extract was subjected to distillation at reduced pressure to recover 11.5 g of the unreacted material (at 100° to 118° C. and 3 mmHg). The residue was purified with methanol to give 41.2 g of pale yellow needle-like crystals, methyl 5-bromo-3-propionylsalicylate, M.P. 106.0° to 108.0° C. in a yield of 95.5% based on the consumed amount of the methyl 5-bromosalicylate. The results of the chemical analysis are shown in Table 2 below.

(b) Synthesis of 5-bromo-3-propionylsalicyclic acid

The methyl 5-bromo-3-propionylsalicyclic acid obtained above in (a) was hydrolyzed to give 5-chloro-3-propionylsalicylic acid which was chemically analyzed with the results shown in Table 2 below.

EXAMPLE 4

Synthesis of dimethylaminoethyl 5-chloro-3-propionylsalicylate

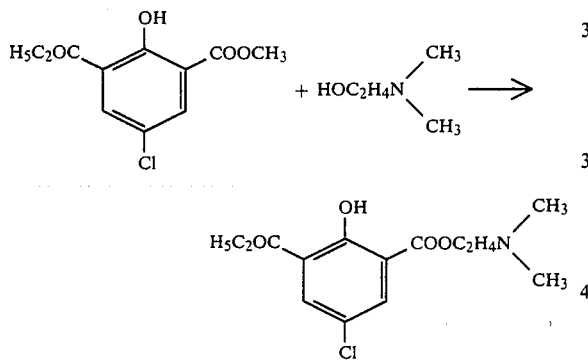

24.3 g (0.10 mole) quantity of methyl 5-chloro-3-propionylsalicylate was added to a solution of 0.5 g (0.022 mole) of sodium in 300 ml of dimethylaminoethanol. The mixture was maintained at room temperature for 24 hours and was heated at 90° C. for 2 hours. The reaction mixture was subjected to distillation to remove the excess unreacted dimethylaminoethanol and the methanol produced, and the residue was recrystallized from cyclohexane to obtain 24.2 g (80.7%) of crystals which melt at 48.5° to 51.0° C. The hydrochloride of the product melts at 148.8° to 151.2° C. and the results of chemical analysis are shown in Table 1 below.

EXAMPLE 5

Synthesis of morpholinoethyl 5-chloro-3-propionylsalicylate

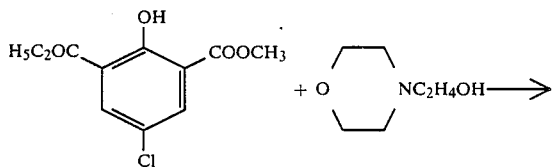

-continued

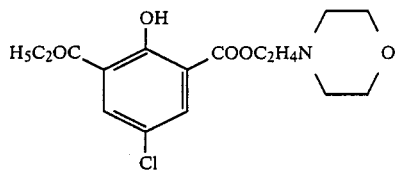

A 24.3 g (0.10 mole) quantity of methyl 5-chloro-3-propionylsalicylate was added to a solution of 0.5 g (0.022 mole) of sodium in 300 ml of morpholinoethanol. The mixture was maintained at room temperature for 24 hours and was heated at 2 hours at 90° C. The reaction mixture was subjected to distillation at reduced pressure to remove the excess unreacted morpholinoethanol and the methanol produced, and the residue was recrystallized from cyclohexane to obtain 38.0 g (88.8%) of crystals which melt at 144.0° to 146.3° C. The chemical analysis of the product was performed with the results shown in Table 1 below.

EXAMPLE 6

Synthesis of β-piperidinoethyl 5-chloro-3-propionylsalicylate

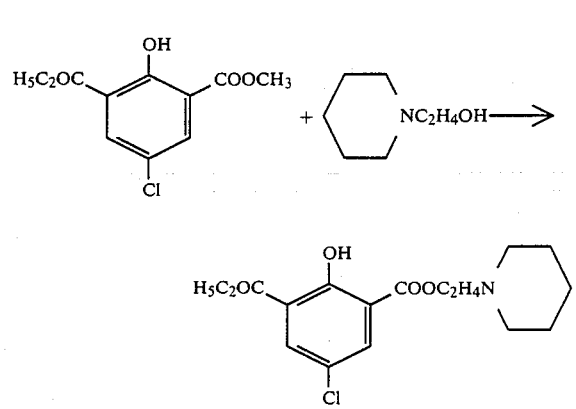

A 24.3 g (0.10 mole) quantity of methyl 5-chloro-3-propionylsalicylate was added to a solution of 0.20 g (0.013 mole) of sodium in 300 ml of piperidinoethanol. The mixture was maintained at room temperature for 24 hours and was heated at 90° C. for 2 hours. The reaction mixture was subjected to distillation at reduced pressure to remove the excess unreacted piperidinoethanol and the methanol produced. The residue was dissolved in dilute hydrochloric acid for purification and was neutralized with sodium carbonate. The separated crystals were collected, washed with water and dried, giving 31.5 g of the contemplated product in a 92.8% yield. The hydrochloride of the product was found to have a melting point of 165.6° to 168° C. The results of chemical analysis are shown in Table 1 below.

EXAMPLE 7

Synthesis of dimethylaminoethyl 5-bromo-3-propionylsalicylate

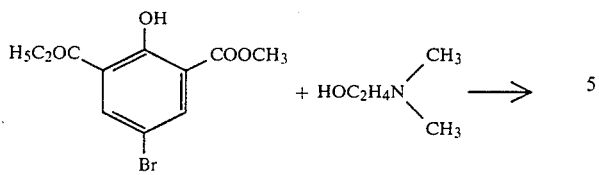

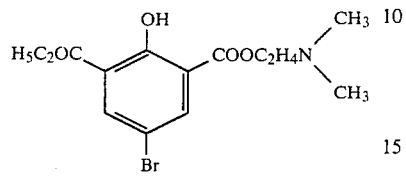

The same procedure as in Example 4 was repeated with the exception of using 28.7 g (0.10 mole) of methyl 5-bromo-3-propionylsalicylate in place of methyl 5-chloro-3-propionylsalicylate, affording 28.0 g (81.4%) of crystals. The hydrochloride of the product melts at 106.6° to 108.0° C. The results of chemical analysis are shown in Table 2 below.

EXAMPLE 8

Synthesis of morpholinoethyl 5-bromo-3-propionylsalicylate

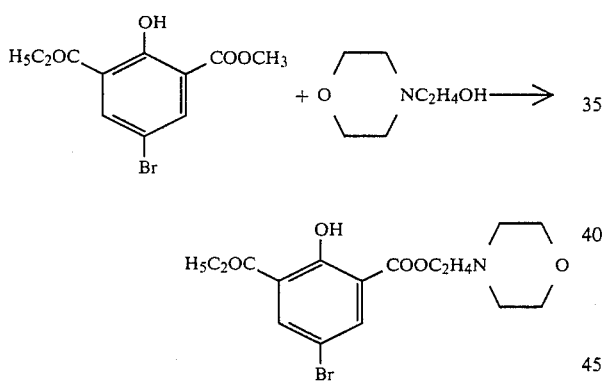

The procedure of Example 5 was repeated with the exception of using 28.7 g (0.10 mole) of methyl 5-bromo-3-propionylsalicylate in place of methyl 5-chloro-3-propionylsalicylate, giving 33.0 g (85.5%) of crystals. The hydrochloride of the product melts at 218.2° to 219.6° C. The results of chemical analysis are shown in Table 2 below.

EXAMPLE 9

Synthesis of β-piperidinoethyl 5-bromo-3-propionylsalicylate

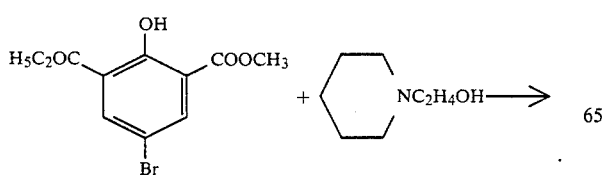

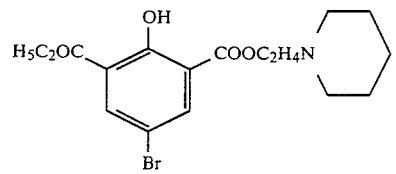

The procedure of Example 6 was repeated with the exception of using 28.7 g (0.10 mole) of methyl 5-bromo-3-propionylsalicylate in place of methyl 5-chloro-3-propionylsalicylate, affording 34.5 g (89.8%) of crystals. The hydrochloride of the product melts at 156.0° to 158.2° C. The results of chemical analysis are shown in Table 2 below.

EXAMPLE 10

Synthesis of dimethylaminoethyl 3-propionylsalicylate

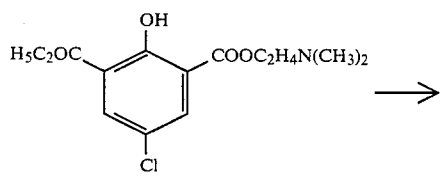

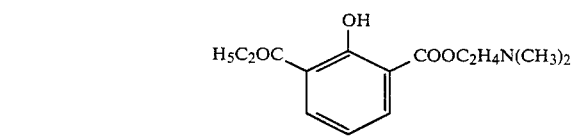

Into a pressure reactor were placed 15.0 g (0.05 mole) of dimethylaminoethyl 5-chloro-3-propionylsalicylate, 10.0 g (0.075 mole) of sodium acetate, 150 ml of methanol and 0.6 g of a 5% palladium-carbon catalyst. After the atmosphere was replaced with hydrogen gas, reaction was conducted at a pressure of 3.0 kg/cm²G at 30° C. for 3 hours. Thereafter the catalyst was removed by filtration and the solvent was recovered. The residue was washed with water and dried, giving 26.0 g of solids. The solids were recrystallized from cyclohexane to provide 22.6 g (85.2%) of the contemplated compound. The hydrochloride of the compound melts at 168.2° to 169.6° C. and was subjected to chemical analysis with the results shown in Table 1 given below.

EXAMPLE 11

Synthesis of morpholinoethyl 3-propionylsalicylate

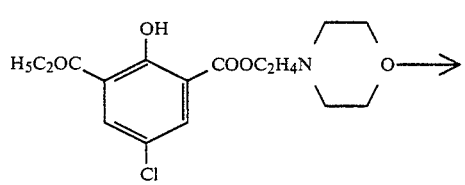

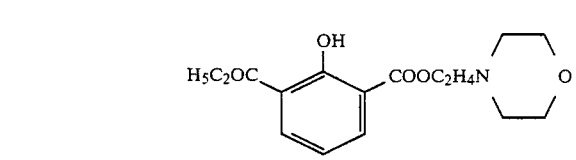

Into a pressure reactor were placed 17.1 g (0.05 mole) of morpholinoethyl 5-chloro-3-propionylsalicylate, 10.0 g (0.075 mole) of sodium acetate, 150 ml of methanol and 0.7 g of a 5% palladium-carbon catalyst. After the atmosphere was replaced with hydrogen gas, reaction was performed at a pressure of 3.0 kg/cm$^2$G at 30° C. for 3 hours. Thereafter the catalyst was filtered off and the solvent was removed by distillation, giving 15.2 g (99.0%) of a crude product. The product was recrystallized from ligroin, affording 12.9 g (84.0%) of white crystals. The crystals were dissolved in benzoyl and hydrogen chloride was forced into the solution to form crystals of hydrochloride melting at 204.5° to 206.0° C. The compound was chemically analyzed with the results shown in Table 1 below.

EXAMPLE 12

Synthesis of β-piperidinoethyl 3-propionylsalicylate

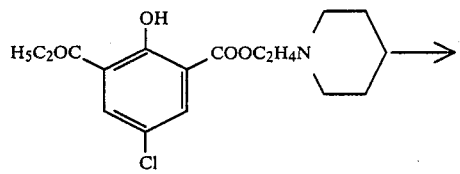

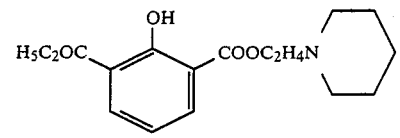

Into a pressure reactor were charged 6.8 g (0.02 mole) of β-piperidinoethyl 5-chloro-3-propionylsalicylate, 5.3 g (0.04 mole) of sodium acetate, 150 ml of methanol and 0.34 g of a 5% palladium-carbon catalyst. After the atmosphere was replaced with hydrogen gas, reaction was carried out at a pressure of 5 kg/cm$^2$G at 40° C. for 5 hours. Thereafter the catalyst was filtered off and the solvent was distilled off, giving 5.9 g (96.7%) of crystals. The crystals were recrystallized from alcohol to provide white crystals from which the hydrochloride of the product was obtained in a usual manner with a melting point of 170.0° to 171.5° C. Table 1 below shows the results of chemical analysis.

TABLE 1

| Ex. | Solvent | NMR spectrum δ value (ppm) | IR spectrum (KBr, cm$^{-1}$) | MASS spectrum (m/e) | Elementary analysis Calcd. | Found |
|---|---|---|---|---|---|---|
| 1a | CDCl$_3$ | 7.99 (s, 2H), 4.02 (s, 3H), 3.11 (q, 2H), 1.19 (t, 3H) | 3350 1695–1690 | 244,242 (Molecular peak) | C$_{11}$H$_{11}$O$_4$Cl C: 54.45% H: 4.57% Cl: 14.61% | C: 54.40% H: 4.56% Cl: 14.60% |
| 1b | DMSO-d$_6$ | 8.19 (d, 1H), 8.11 (d, 1H), 3.10 (q, 2H), 1.10 (t, 3H) | 3400 3100–3000 1690–1685 | 230,228 (Molecular peak) | C$_{10}$H$_9$O$_4$Cl C: 52.53% H: 3.97% Cl: 15.51% | C: 52.51% H: 3.94% Cl: 15.50% |
| 2 | DMSO-d$_6$ | 8.26 (br. s, 2H), 4.56 (q, 2H), 3.21 (q, 2H), 1.40 (t, 3H), 1.13 (t, 3H) | 3350 1695 | 258,257 (Molecular peak) | C$_{12}$H$_{13}$O$_4$Cl C: 56.15% H: 5.10% Cl: 13.81% | C: 56.14% H: 5.10% Cl: 13.78% |
| 4 | DMSO-d$_6$ | 8.51 (d, 1H), 8.24 (d, 1H), 4.95–4.75 (m, 2H), 3.85 (t, 2H), 3.25 (q, 2H), 2.96 (s, 3H), 2.87 (s, 3H), 1.13 (t, 3H) | 3380 1710 | 292,290 (Molecular peak) | C$_{14}$H$_{19}$O$_4$NCl$_2$ C: 50.01% H: 5.70% N: 4.17% Cl: 21.09% | C: 49.96% H: 5.63% N: 4.18% Cl: 21.05% |
| 5 | CDCl$_3$ | 7.88 (d, 1H), 7.76 (d, 1H), 4.82–4.56 (m, 2H), 3.96 (t, 2H), 3.44–2.76 (m, 8H), 3.02 (q, 2H), 1.18 (t, 3H) | 3400 1720 | 343,341 (Molecular peak) | C$_{16}$H$_{20}$O$_5$NCl C: 56.23% H: 5.90% N: 4.10% Cl: 10.37% | C: 56.20% H: 5.79% N: 4.08% Cl: 10.35% |
| 6 | DMSO-d$_6$ | 8.40 (d, 1H), 8.24 (d, 1H), 5.00–4.80 (m, 2H), 3.94 (t, 2H), 3.22 (q, 2H), 3.60–3.20 (m, 4H), 2.18–1.48 (m, 6H), 1.14 (t, 3H) | 3400 1700 | 343,340 (Molecular peak) | C$_{17}$H$_{23}$O$_4$NCl$_2$ C: 54.26% H: 6.16% N: 3.72% Cl: 18.84% | C: 54.22% H: 6.13% N: 3.74% Cl: 18.80% |
| 10 | DMSO-d$_6$ | 8.66 (d, 1H), 8.37 (d, 1H), 7.33 (d, 1H), 5.07–4.81 (m, 2H), 3.86–3.68 (m, 2H), 3.33 (q, 2H), 2.99 (s, 6H) | 3400 1700 1640 | 266 (Molecular peak) | C$_{14}$H$_{20}$O$_4$NCl C: 55.72% H: 6.68% N: 4.64% Cl: 11.75% | C: 55.69% H: 6.65% N: 4.63% Cl: 11.71% |
| 11 | DMSO-d$_6$ | 8.46 (t, 2H), 7.34 (t, 1H), 5.06–4.86 (m, 2H), 4.28–4.02 (m, 4H), 3.86–3.46 (m, 6H), 3.26 (q, 2H), 1.16 (t, 3H) | 3400 1730 1645 | 308 (Molecular peak) | C$_{16}$H$_{22}$O$_5$NCl C: 55.90% H: 6.45% N: 4.07% Cl: 10.31% | C: 55.88% H: 6.43% N: 4.03% Cl: 10.32% |
| 12 | DMSO-d$_6$ | 8.43 (t, 2H), 7.34 (t, 1H), 5.04–4.84 (m, 2H), 3.86–3.40 (m, 6H), 3.24 (q, 2H), 2.20–1.60 (m, 6H), 1.15 (t, 3H) | 3360 1735 1650 | 306 (Molecular peak) | C$_{17}$H$_{24}$O$_4$NCl C: 59.73% H: 7.08% N: 4.10% Cl: 10.37% | C: 59.71% H: 7.02% N: 4.10% Cl: 10.33% |

TABLE 2

| Ex. | Solvent | NMR spectrum δ value (ppm) | IR spectrum (KBr, cm$^{-1}$) | MASS spectrum (m/e) | Elementary analysis Calcd. | Found |
|---|---|---|---|---|---|---|
| 3a | DMSO-d$_6$ | 8.58 (s, 2H), 4.20 (s, 3H), 3.29 (q, 2H), 1.20 (t, 3H) | 3400 1690–1665 | 288, 286 (Molecular peak) | C$_{11}$H$_{11}$O$_4$Br C: 46.02% H: 3.86% Br: 27.83% | C: 45.97% H: 3.79% Br: 27.90% |
| 3b | DMSO-d$_6$ | 13.40–13.20 (br. s, 1H), 8.13 (d, 1H), 8.02 (d, 1H), 3.08 (q, 2H) | 3600–2700 1695–1660 | 272, 274 (Molecular peak) | C$_{10}$H$_9$O$_4$Br C: 43.98% H: 3.32% Br: 29.26% | C: 44.01% H: 3.35% Br: 29.31% |
| 7 | DMSO-d$_6$ | 8.68 (d, 1H), 8.48 (d, 1H), 5.12–4.90 (m, 2H), 3.90–3.68 (m, 2H), 3.28 (q, 2H), 2.98 (s, 6H), 1.18 (t, 3H) | 3450–3400 1685–1675 | 344, 346 (Molecular peak) | C$_{14}$H$_{18}$BrNO$_4$HCl C: 44.17% H: 5.03% N: 3.68% Cl: 9.31% Br: 20.99% | C: 44.21% H: 5.05% N: 3.71% Cl: 9.30% Br: 21.00% |
| 8 | DMSO-d$_6$ | 8.73 (d, 1H), 8.53 (d, 1H), 5.16–4.95 (m, 2H), 4.36–4.06 (m, 4H), 3.86–3.64 (m, 2H), 3.62–3.40 (m, 4H), 3.24 (q, 2H), 1.18 (t, 3H) | 3420 1685–1675 | 388, 386 (Molecular peak) | C$_{16}$H$_{21}$O$_5$NClBr C: 45.46% H: 5.01% N: 3.31% Cl: 8.39% Br: 18.90% | C: 45.41% H: 5.05% N: 3.28% Cl: 8.41% Br: 18.89% |
| 9 | DMSO-d$_6$ | 8.60 (d, 1H), 8.48 (d, 1H), 5.08–4.86 (m, 2H), 3.92–3.71 (m, 2H), 3.64–3.48 (m, 4H), 3.22 (q, 2H), 2.34–1.65 (m, 6H), 1.18 (t, 3H) | 3450–3350 1685–1675 | 384, 386 (Molecular peak) | C$_{17}$H$_{23}$O$_4$BrNCl C: 48.53% H: 5.51% N: 3.33% Cl: 8.43% Br: 18.99% | C: 48.59% H: 5.54% N: 3.31% Cl: 8.45% Br: 18.97% |

EXAMPLE 13

Synthesis of dimethylaminoethyl 3-propionylsalicylate

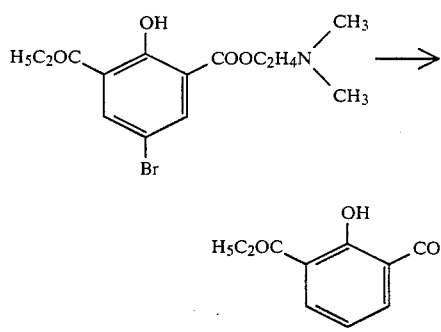

The same procedure as in Example 10 was repeated with the exception of using 17.2 g (0.05 mole) of dimethylaminoethyl 5-bromo-3-propionylsalicylate in place of dimethylaminoethyl 5-chloro-3-propionylsalicylate, giving 11.2 g (84.5%) of a product. The hydrochloride of the product was found to have a melting point of 168.2° to 169.6° C.

EXAMPLE 14

Synthesis of morpholinoethyl 3-propionylsalicylate

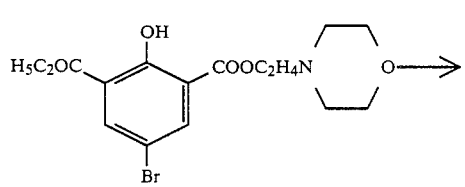

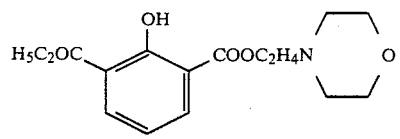

The procedure of Example 11 was repeated with the exception of using 19.3 g (0.05 mole) of morpholinoethyl 5-bromo-3-propionylsalicylate in place of morpholinoethyl 5-chloro-3-propionylsalicylate, producing 13.1 g (85.3%) of a product. The hydrochloride of the product was found to have a melting point of 204.5° to 206° C.

EXAMPLE 15

Synthesis of β-piperidinoethyl 3-propionylsalicylate

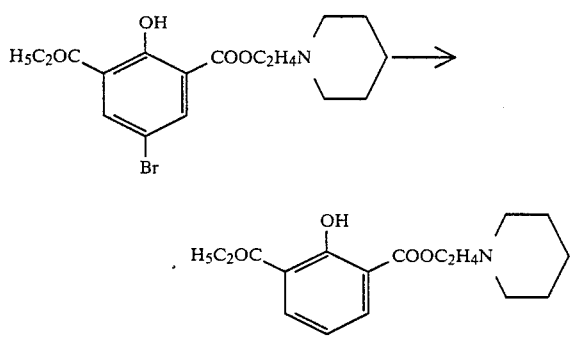

The procedure of Example 12 was followed with the exception of using 7.7 g (0.02 mole) of β-piperidinoethyl 5-bromo-3-propionylsalicylate in place of β-piperidinoethyl 5-chloro-3-propionylsalicylate, giving 5.8 g (95.0%) of a product. The hydrochloride of the product had a melting point of 170.0 to 171.5° C.

EXAMPLE 16

(a) Synthesis of methyl 3-propionylsalicylate

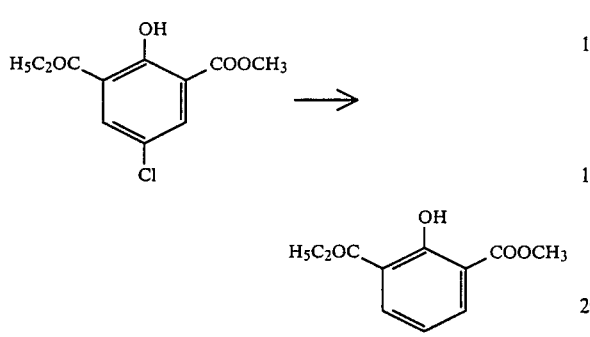

Into a pressure reactor were placed 10 g (0.041 mole) of methyl 5-chloro-3-propionylsalicylate, 8.3 g (0.062 mole) of sodium acetate, 150 ml of methanol and 0.6 g of a 5% palladium-carbon catalyst. After the atmosphere was replaced with hydrogen gas, reaction was conducted at a pressure of 3.0 kg/cm²G at 30° C. for 3 hours. Thereafter the catalyst was filtered off and the solvent was distilled off from the filtrate to give 8.4 g (97.9%) of a crude product. The product was recrystallized from ligroin to afford 7.7 g (89.8%) of white needle-like crystals, M.P. 43° to 44° C.

A 7.7 g quantity of white needle-like crystals identical with those obtained above in (a) was produced in the same manner as above with the exception of using 11.8 g (0.041 mole) of methyl 5-bromo-3-propionylsalicylate in place of methyl 5-chloro-3-propionylsalicylate. Yield 90.3%. M.P. 43° to 44° C.

(b) Synthesis of β-piperidinoethyl 3-propionylsalicylate

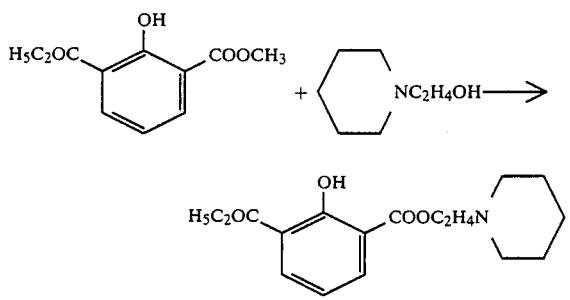

A 20.8 g (0.10 mole) quantity of methyl 3-propionylsalicylate was added to a solution of 0.5 g (0.022 mole) of sodium in 300 ml of piperidinoethanol. The mixture was maintained at room temperature for 24 hours and then was heated at 90° C. for 2 hours. Thereafter the excess piperidinoethanol and the methanol produced were distilled off at reduced pressure. The residue was recrystallized from ligroin to provide 26.8 g (87.8%) of crystals. The hydrochloride of the product had a melting point of 170.0° to 171.5° C. The product was found identical with that obtained in Example 12. The two products were melted together and showed a melting point not lower than that of each product.

REFERENCE EXAMPLE 3

Synthesis of β-piperidinoethyl 3-methylflavone-8-carboxylate

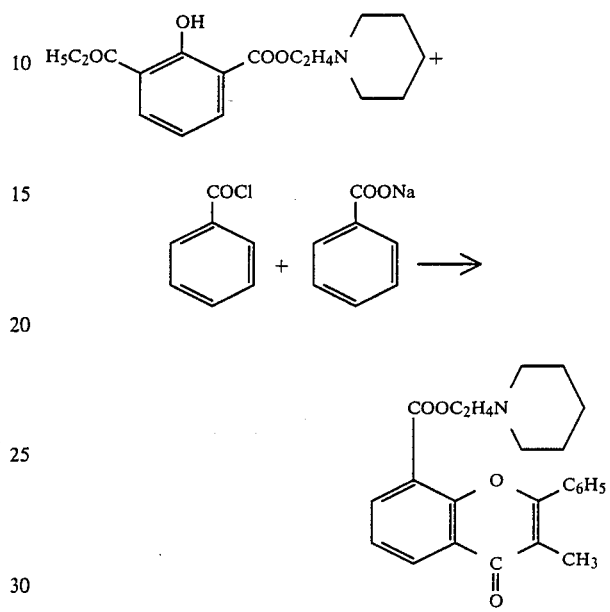

A 14.4 g (0.1 mole) quantity of sodium benzoate was added with stirring to a mixture of 9.2 g (0.03 mole) of β-piperidinoethyl 3-propionylsalicylate and 12.6 g (0.09 mole) of benzoyl chloride. The mixture was heated in an oil bath at 180° to 190° C. for 8 hours. To the cooled reaction mixture was added an aqueous solution of sodium carbonate and the mixture was stirred to form a precipitate. The solids were filtered off and purified with alcohol to give 10.7 g (90.7%) of a product melting at 85° to 86° C. The melting point of the hydrochloride of the product was 232° to 234° C.

REFERENCE EXAMPLE 4

Synthesis of morpholinoethyl 6-bromo-3-methylflavone-8-carboxylate

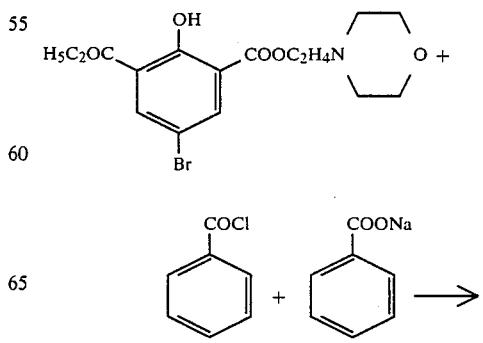

-continued

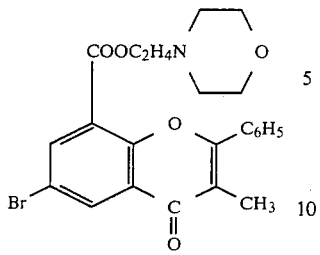

A 23.7 g (0.165 mole) quantity of sodium benzoate was added to a mixture of 19.3 g (0.05 mole) of morpholinoethyl 5-bromo-3-propionylsalicylate and 21.1 g (0.15 mole) of benzoyl chloride. The resulting mixture was heated in an oil bath at 180° to 190° C. for 8 hours. To the cooled reaction mixture was added a 10% hydrochloric acid solution to dissolve the mixture therein. The insolubles were separated from the mixture and the residue was neutralized with soda ash. Crystals precipitated were collected and dried. A product was obtained in an amount of 21.0 g in 89.0% yield. The hydrochloride of the product was found to melt at 205.0° to 208.0° C.

REFERENCE EXAMPLE 5

Synthesis of dimethylaminoethyl 6-bromo-3-methylflavone-8-carboxylate

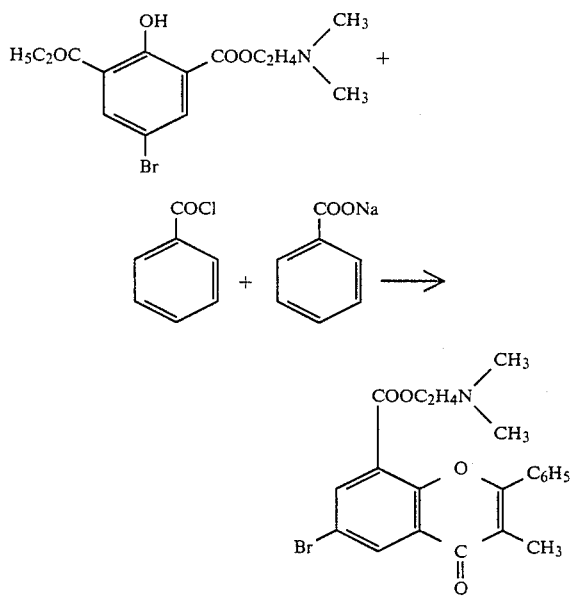

A 47.5 g (0.33 mole) quantity of sodium benzoate was added to a mixture of 34.4 g (0.1 mole) of dimethylaminoethyl 5-bromo-3-propionylsalicylate and 42.1 g (0.30 mole) of benzoyl chloride. The resulting mixture was heated in an oil bath at 180° to 190° C. for 8 hours. To the cooled reaction mixture was added dilute hydrochloric acid to dissolve the mixture therein. After the insolubles were separated from the solution, the residue was neutralized with soda ash and solids thus precipitated were extracted with chloroform. The solvent was separated to give 38.0 g (88.3%) of crystals. The hydrochloride of the product had a melting point of 192.0° to 195.4° C.

We claim:

1. A derivative of 3-propionylsalicylic acid represented by the formula (1)

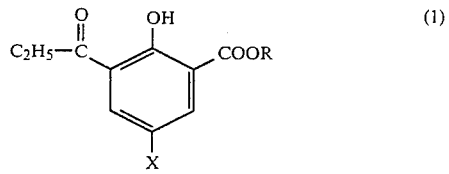

wherein R represents a hydrogen atom, a lower alkyl group or a group

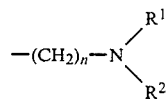

(wherein $R^1$ and $R^2$ represent a lower alkyl group or $R^1$ and $R^2$, when taken together with the nitrogen atom to which they are attached, may form a heterocyclic ring with or without an intervening hetero atom, and n is an integer of 1 to 4), and X represents a hydrogen atom or a halogen atom, R being the group

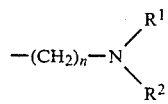

when X is a hydrogen atom.

2. A compound as defined in claim 1 wherein X is a halogen atom.
3. A compound as defined in claim 2 wherein the halogen atom is chlorine or bromine.
4. A compound as defined in claim 1 wherein X is a hydrogen atom.
5. A compound as defined in claim 2 or 3 wherein R is a hydrogen atom.
6. A compound as defined in claim 2 or 3 wherein R is a lower alkyl group.
7. A compound as defined in claim 6 wherein the lower alkyl group is methyl or ethyl.
8. A compound as defined in claim 2 or 3 wherein R is a group

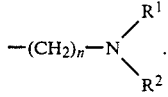

9. A compound as defined in claim 8 wherein $R^1$ and $R^2$ are lower alkyl groups.
10. A compound as defined in claim 9 wherein the lower alkyl groups are methyl.
11. A compound as defined in claim 8 wherein the group

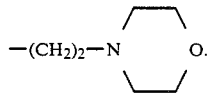

* * * * *